United States Patent
Ali et al.

[11] Patent Number: 6,101,234
[45] Date of Patent: Aug. 8, 2000

[54] APPARATUS AND METHOD FOR DISPLAYING COMPUTED TOMOGRAPHY FLUOROSCOPY IMAGES

[75] Inventors: Fazle Ali; Jiang Hsieh, both of Brookfield; Girish Saligram, Waukesha; Shawn P. Faessler, New Berlin; Christopher J. Mussack, Waukesha; David M. Deaven, Waukesha; Stanley H. Fox, Brookfield; Alexsandar Zavaljevski, Waukesha, all of Wis.

[73] Assignee: General Electric Company, Milwaukee, Wis.

[21] Appl. No.: 08/978,803

[22] Filed: Nov. 26, 1997

[51] Int. Cl.[7] .................................................. A61B 6/03
[52] U.S. Cl. .................................................. 378/4; 378/901
[58] Field of Search .................................. 378/4, 15, 901

[56] References Cited

U.S. PATENT DOCUMENTS

| | | | |
|---|---|---|---|
| 5,371,778 | 12/1994 | Yanof et al. | 378/4 |
| 5,708,690 | 1/1998 | Hsieh | 378/4 |

*Primary Examiner*—David V. Bruce
*Attorney, Agent, or Firm*—Armstrong Teasdale; Christian G. Cabou; Phyllis Y. Price

[57] ABSTRACT

A CT Fluoro System display which includes apparatus and methods for facilitating effective performance of an interventional procedure. The apparatus and methods are generally referred to herein as partial image display, dynamic image reformation, in-room control, flat panel display, in-room display, and magnification. More particularly, an important performance parameter for a CT Fluoro System is the time to first image. Accordingly, and to reduce the time to first image, a partially reconstructed image can be displayed. In addition to fast image reconstruction, it sometimes is necessary to examine a needle position from different orientations, i.e., views. Accordingly, the present display provides dynamic image reformation wherein axial images are displayed at a very high rate and the operator may reformat the axial images and display the reformatted images in real time. Further, and to provide additional functionality and convenience for an operator, an in-room, or convenient, control including a "reverse and forward" play command button, "save" (or capture), "grid display", and "preset window/levels" functions is provided. By enabling an operator to perform these functions with the remote unit, the system is believed to be easier to use and useful information to the operator in an easily understandable format. Also, and to provide improved display, a flat panel display may be utilized. A user interface for use with the display includes a CT/i Interventional control, three message areas (hierarchical and designated as message area #1, message area #2, and message area #3), and an image control. Also, image magnification can be performed.

20 Claims, 2 Drawing Sheets

APPARATUS AND METHOD FOR DISPLAYING COMPUTED TOMOGRAPHY FLUOROSCOPY IMAGES

FIELD OF THE INVENTION

This invention relates generally to computed tomography (CT) imaging and more particularly, to enhancing the display of images during CT fluoroscopy scans.

BACKGROUND OF THE INVENTION

In at least one known CT system configuration, an x-ray source projects a fan-shaped beam which is collimated to lie within an X-Y plane of a Cartesian coordinate system, generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object.

One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved in the z-axis synchronously with the rotation of the gantry, while the data for the prescribed number of slices is acquired. Such a system generates a single helix from a fan beam helical scan. The helix mapped out by the fan beam yields projection data from which images in each prescribed slice may be reconstructed. In addition to reduced scanning time, helical scanning provides other advantages such as better control of contrast, improved image reconstruction at arbitrary locations, and better three-dimensional images.

In CT fluoroscopic systems ("CT Fluoro"), sequential frames of images are generated to help, for example, in guiding a needle to a desired location within a patient. A frame, like a view, corresponds to a two dimensional slice taken through the imaged object. Particularly, projection data is processed at a high frame rate to construct an image frame of the object.

With known CT Fluoro systems, the general objective is to provide the physician with as much useful information as quickly as possible to guide the procedure. For example, one important parameter in CT Fluoro systems in the "time to first image", i.e., the lag time between x-ray turned on and the first frame. Reducing the time to the first image provides the operator with a better sense of the situation. In addition, the information should be displayed and retrievable in a format definable by the physician.

It would be desirable to improve CT support for interventional procedures. Particularly, it would be desirable to acquire data, reconstruct such data and display an image for such data quickly enough to guide an interventional procedure. It also would be desirable to improve the image display for interventional procedures.

SUMMARY OF THE INVENTION

These and other objects may be attained by a CT Fluoro System display which includes apparatus and methods for facilitating effective performance of an interventional procedure. The apparatus and methods are generally referred to herein as partial image display, dynamic image reformation, in-room control, flat panel display, and in-room display. More particularly, an important performance parameter for a CT Fluoro System is the time to first image. By generating a first image more quickly, the operator is provided with more information and should have a better sense of control since timely feedback is provided. Accordingly, and to reduce the time to first image, a partially reconstructed image can be displayed. For example, a set of images can be produced using ⅙ to ⅚ of the full views and overscan weights. The views can be displayed at roughly a rate of 6 frames per second.

In addition to fast image reconstruction, it sometimes is necessary to examine a needle position from different orientations, i.e., views. Accordingly, the present display provides dynamic image reformation wherein axial images are displayed at a very high rate and the operator may reformat the axial images and display the reformatted images in real time. The operator may therefore view the needle from different angles and obtain depth information.

Further, and to provide additional functionality and convenience for an operator, an in-room, or convenient, control including a "reverse and forward" play command button, "save" (or capture), "grid display", and "preset window/levels" functions is provided. By enabling an operator to perform these functions with the remote unit, the system is believed to be easier to use and useful information to the operator in an easily understandable format.

Also, and to provide improved display, a flat panel display may be utilized. The display, in one embodiment has a 1280×1024 pixel configuration, good image resolution, and has about a 15"–17" diagonal size. The display may, of course, be smaller or larger. The display is ceiling suspended and located at the gantry perimeter for access to the display from front/back and right/left sides. The suspension system allows four axis of positionability and can be positioned close in the gantry bore area. The suspension system also is counter poised for easy placement/adjustment by an operator, and can be moved quickly for access to a patient.

A user interface for use with the display includes a CT/i Interventional control, three message areas (hierarchical and designated as message area #1, message area #2, and message area #3), and an image control. The interventional control enables the operator to analyze and manipulate images for view on the display. Messages are displayed in the respective message areas. The most urgent messages are displayed in area #1, less urgent messages are displayed in area #2, and the least urgent messages are displayed in area

3. The image control includes page forward and page backward commands, forward 1 image and backup 1 image commands, and a capture command which enables an operator to save the image then displayed on the screen to the display memory buffer or database. The captured images can be recalled for display, analysis, filming, archiving, and networking.

DETAILED DESCRIPTION

Figure 1:
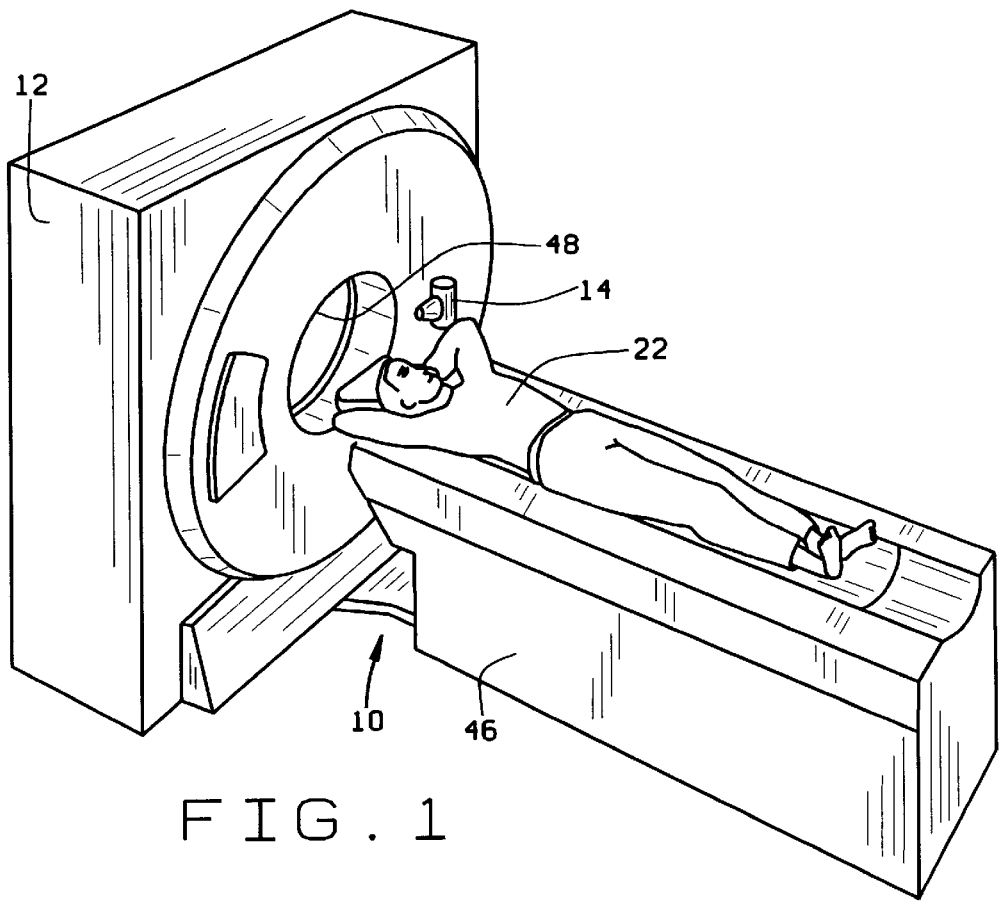
FIG. 1 is a pictorial view of a CT imaging system.
Figure 2:
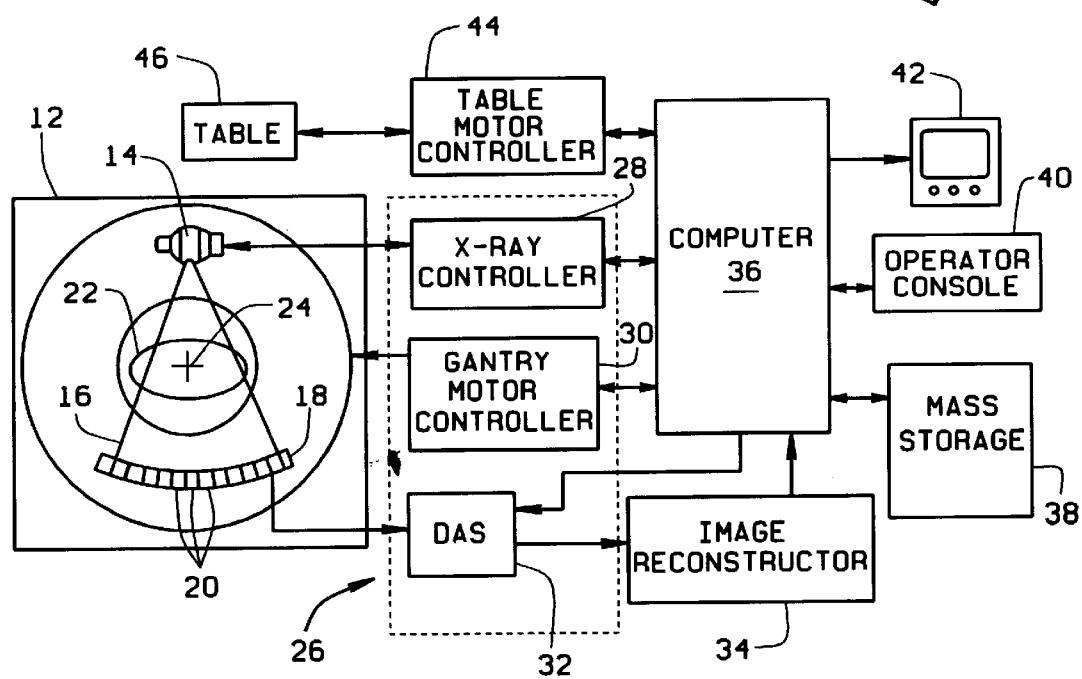
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. The present invention is not limited to practice in connection with third generation scanners and can be used, for example, in fourth generation scanners and in CT electron beam type scanners. Therefore, although the present invention is sometimes described herein in connection with third generation scanners, it should be understood that such description is by way of example only, and not by way of limitation.

With respect to system 10, gantry 12 has an x-ray source 14 that projects a beam of x-rays 16 through a source collimator (not shown) and at a gantry angle (not shown) toward a detector array 18 on the opposite side of gantry 12. Detector array 18 is formed by detector elements 10 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38. Preferably, the reconstructed image is stored as a data array.

Computer 36 also receives commands and scanning parameters from an operator via console 40 that has a keyboard. An associated display 42, such as a flat panel or a cathode ray tube display, allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48. As used herein, an Xmm by Xmm scan refers to scanning an object of interest using an X mm collimator aperture at a 1:1 helical pitch, wherein helical pitch is the ratio of table 46 movement in one rotation of the x-ray source 14 to the slice width defined by the source collimator.

The following description sets forth details regarding various display apparatus and methods that can be practiced in CT Fluoro and other applications to provide operators with enhanced display options. The apparatus and methods are referred to below as partial image display, dynamic image reformation, in-room control, flat panel display, and in-room display. Each of these apparatus and methods can be practiced by themselves in a CT Fluoro System, or in any combination, to provide the desired operational results.

A. Partial Image Display

As explained above, an important performance parameter for a CT Fluoro System is the time to first image. By generating a first image more quickly, the operator is provided with more information and should have a better sense of control since timely feedback is provided. Accordingly, and to reduce the time to first image, a partially reconstructed image can be displayed. For example, a set of images can be produced using $\frac{1}{6}$ to $\frac{5}{6}$ of the full views and overscan weights. The views can be displayed at roughly a rate of 6 frames per second. In one specific system, the partially reconstructed images can be displayed when 120, 232, 352, 464, and 584 views are accumulated in the first image generation memory buffer. The overscan algorithm may, for example, be the overscan algorithm described in copending U.S. patent application Ser. No. (15-CT-4313), entitled Image Reconstruction In A Computed Tomography Fluoroscopy System, which is assigned to the present assignee and incorporated herein, in its entirety, by reference. The overscan angle may, for example, be 22.0 degrees.

Generally, the partially reconstructed image is obtained with the weighting scheme. Since most of the motion artifact suppression weights (e.g., overscan weights) suppress the contribution from the start of the scan and gradually increase the contribution of the views to the final image, overscan weighting presents a smoother transition from image to image as the partially reconstructed images are displayed, as compared to no weights. Of course, other weighting schemes can be used.

B. Dynamic Image Reformation

Examining the needle position from different orientations, i.e., views, sometimes is desired. To address this need, dynamic image reformation can be performed. Particularly, axial images are displayed at a very high rate and the operator may reformat the axial images and display the reformatted images in real time. The operator may therefore view the needle from different angles and obtain depth information.

The image reformation may be performed by image interpolation. Particularly, image reformation refers to viewing a cut-through plane of an object. That is, in a conventional CT display, a series of images perpendicular to the z-axis are generated and displayed. If the same object is desired to be viewed along a plane that is in alignment with the z-axis which forms a 45 degree angle with the x-y axis, then the intersection of this new plane with the set of planes that represent the CT image is determined. Once the intersections are determined, a reformatted image can be formed by linear interpolation of the original CT images along the intersections. Image reformation algorithms are known.

C. In-room control

To provide additional functionality and convenience for a user, the following functions can be provided by an in-room control, or convenient, hand held unit. The manner in which commands are communicated from the remote unit to the display are well known in the art. The functions are generally referred to as "reverse and forward", "save" (or capture), "grid display", and "preset window/levels". By enabling an operator to perform these functions with the remote unit, the system is believed to be easier to use and useful information to the operator in an easily understandable format.

The "reverse and forward" function is a double functionality control with a deadman control (push and hold button) and a momentary or single push button. Specifically, when the button is pushed and released as a momentary function, a command to advance or reverse (depending on which button is pushed) one image for each button press is communicated to the display. When the button is pushed and held for more than a pre-defined time, e.g., two seconds, a command to display images in real time, e.g., 6 images per second, forward or backward (depending on the button pressed) will be communicated to the display. The images are stored in a memory buffer (e.g., the last 120 images are stored in the buffer) to enable such function. When the button is released, the play function stops.

The "save" function is a momentary or single push button on the remote unit, and by depressing the save button, a command is transmitted to the display so that the image then displayed on the screen will be captured or saved to the display memory buffer or database. The captured images can be recalled for display, analysis, filming, archiving, and networking.

The "grid display" function is a momentary or single push button. When the grid display button is depressed, a command is transmitted to the display so that a grid pattern scaled in square centimeters is superimposed over the image. Consecutive button pushes activate and deactivate the grid display.

The "preset window/levels" function is a momentary or signal push button. Each time the preset window/levels button is depressed, a command is transmitted to the display to advance one predefined window/level setting. Alternatively, it is contemplated that one button push can cause the window/level setting to change in accordance with preprogrammed or defined settings selected by the operator. It is believe that the by limiting the defined setting to a maximum of 5 to avoid confusion. The setting name and/or values are displayed on the display screen with the image, and the command causes the display to sequence through window/level parameter settings in a continuous loop, advancing one setting with each push of the button. Sequencing typically occurs only in one ordered direction.

Although a hand held unit is described above, the in-room control could be provided by voice activated command device, or the controls can be provided by touching an LED, or hand gestures could be used in combination with a remote sensing device. Therefore, it should be understood that the foregoing description of an in-room control is not limited to practice with a hand held device.

Generally, the functionality that is controllable by a remote control includes, but is not limited to, forward and reverse image review in either fast or slow speed, image save, grid display, and selection of a pre-set of window/level settings. The grid display could be a grid, concentric circles (polar coordinates) at the target, or a ruler along the trajectory of the needle path, or a combination of these displays.

D. Flat Panel Display

To provide improved display, a flat panel display may be utilized. Such displays are commercially available, and one display suitable for use in CT Fluoro systems in Model No. ATC1245B of Allus Technology Corp., 12611 Jones Road, Houston, Tex., 77070. The display, in one embodiment has a 1280×1024 pixel configuration, good image resolution, and has about a 15"–17" diagonal size. The display may, of course, be smaller or larger.

The display is ceiling suspended. Such ceiling suspension system are commercially available, and one suspension system suitable for use in CT Fluoro systems is Model No. 6262 of Mavig, 202 Whistle Stop, Pittsford, N.Y., 14534. The suspension system is located at the gantry perimeter for access to the display from front/back and right/left sides. The suspension system allows four axis of positionability and can be positioned close in the gantry bore area. The suspension system also is counter poised for easy placement/adjustment by an operator, and can be moved quickly for access to a patient. The display also should have a wide viewing angle to accommodate two viewers and should be a color display to provide an enhanced user interface.

E. In-Room Display

Figure 3:
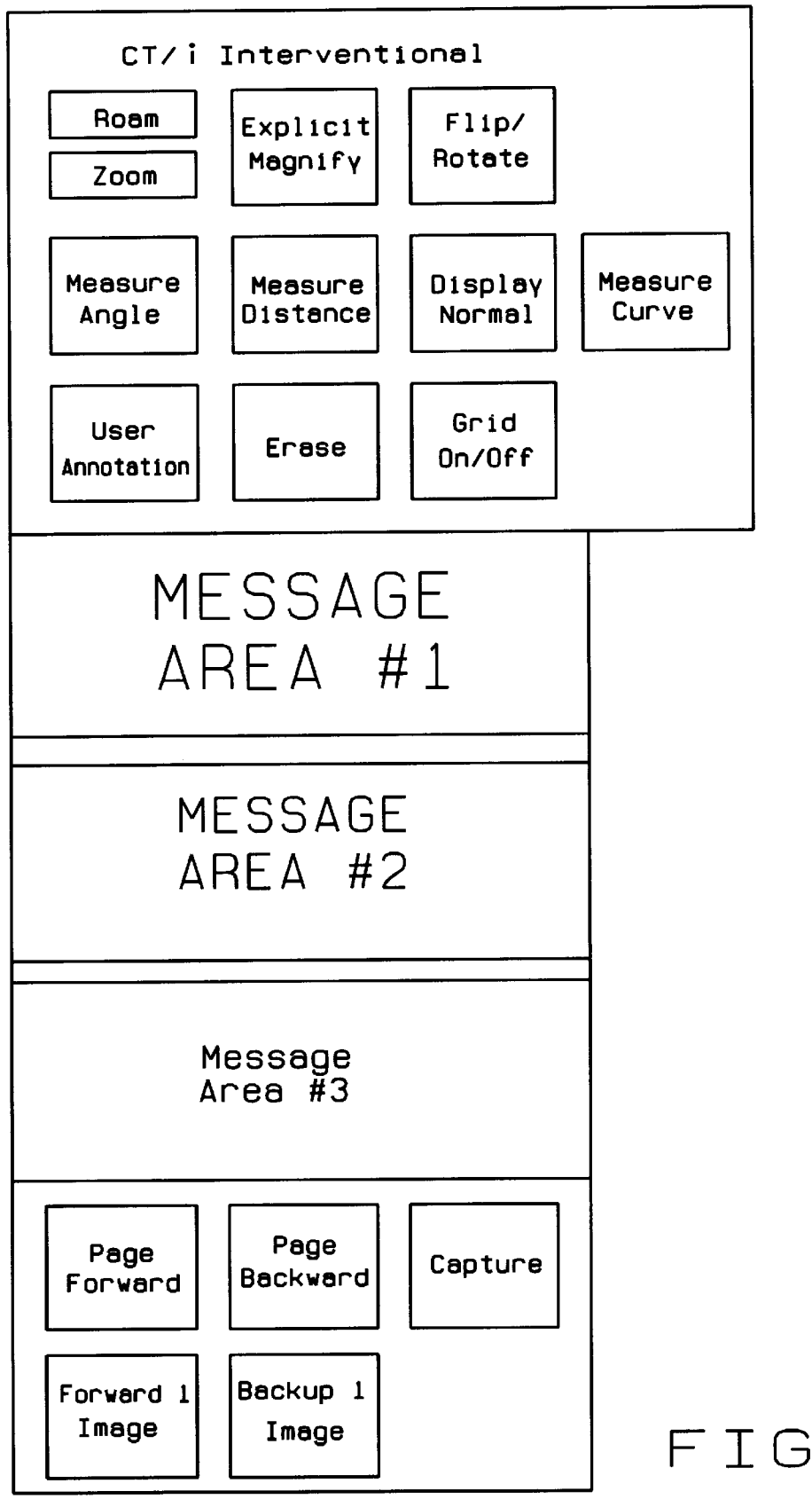
FIG. 3 illustrates a user interface in accordance with one embodiment of the present invention.

A user interface for use with a CT Fluoro system display is illustrated in FIG. 3. Display includes a CT/i Interventional control, three message areas (hierarchical and designated as message area #1, message area #2, and message area #3), and an image control. Interventional control enables the operator to analyze and manipulate images for view on the display. For example, control includes commands for roaming and zooming, for magnifying, and for flipping/rotating an image. Control also includes commands for measuring an angle, distance, and curve. A control command also is provided to return the display to the normal display mode of operation.

Control further includes a command to allow user annotations to be added to an image, and a command to erase annotation. A grid on/off command also is provided which enables a user to have a grid pattern scaled in square centimeters superimposed over the image being displayed.

Messages are displayed in the respective message areas. The most urgent messages are displayed in area #1, less urgent messages are displayed in area #2, and the least urgent messages are displayed in area #3.

Image control includes page forward and page backward commands. The page forward and page backward commands allow the operator to page through the messages displayed in areas #1, #2, and #3 to find the desired message. The forward 1 image and backup 1 image commands enable the operator to select an image for display. The capture command enables an operator to save the image then displayed on the screen to the display memory buffer or database. The captured images can be recalled for display, analysis, filming, archiving, and networking.

The display may also includes two clocks indicating the x-ray exposure time. Particularly, the first clock indicates the exposure during a single run. Whenever the foot switch is initiated, the clock starts to count the number of seconds that the patient is exposed to the x-ray. Specifically, each procedure presently is limited to 90 seconds of exposure, and this first clock helps the operator to better control the patient exposure as well as the timing. The second clock indicates the accumulative exposure time to the patient. For example, during each biopsy operation, multiple x-ray "burst" can be initiated. Between the bursts, the operator will have time to consider the best approach for the next burst. The second clock keeps track of the total amount of exposure performed up to the current time. The clocks serve as indicates that could be either time (length of exposure), total mAs (tube current multiplied by time), or some type of total dose measure to the patient (e.g., organ dose or skin dose) based.

F. Magnification

Real time magnifications of digital images are needed in many applications. Some magnification methods, such as nearest neighbor and bilinear interpolation, are included in general purpose graphic packages and optimized for execution speed on specialized hardware. But higher quality magnification algorithms such as bicubic interpolation are not included. Hence the need arises for methods that approximate bicubic interpolation, but use routines that are accelerated.

As described below in more detail, algorithms for altering the spatial characteristics of digital images can be utilized for such magnification. Generally, one algorithm uses a two pass scheme in which each of the passes represents interpolation in the x and y directions respectively. Bicubic interpolation in each direction is approximated using linear interpolation followed by a one dimensional convolution filter. The other algorithm applies bilinear interpolation first, followed by a two dimensional convolution filter. Note that the order of operation can be reversed. That is, the filtering operation can be applied first followed by the interpolation. The advantage of the reverse order is that the actual area (in terms of mm) covered by the filtering operation is larger. As a result, a smaller filter kernel (e.g., 3×3) covers the same area as a larger kernel in previous case (e.g., 5×5). In addition, before the interpolation, the number of pixels to be filtered is much smaller (256×256 vs. 768×678). The methods can be practiced using the OpenGL graphic package, which is well known in the art. Also, the linear, bilinear, cubic and bicubic interpolations are well known procedures, along with the linear least squares estimation method. By combining linear and bilinear interpolations and digital convolution filters to approximate bicubic interpolation, advantages such as a quickly executable routine are possible. Generally, the algorithms use functions of linear interpolation and digital convolution filters, that are accelerated in OpenGL to approximate the bicubic interpolation. Linear, or bilinear, interpolation is a well defined function. Set forth below are the coefficients of convolution filters to be used in the algorithms.

More particularly, and in the first algorithm, two pass linear interpolation and 1 D filtering is utilized. The first pass performs interpolation in the x direction, and second pass repeats the same procedure for interpolation in the y direction. Interpolations in x and y directions are implemented using identical procedures, and both are performed in two steps. The linear interpolation is performed first, and then the 1 D convolution filter is applied to the interpolated data. The algorithm can be applied for any integer zoom factor n, and for any 1 D convolution filter size m.

To determine the coefficients of the 1 D convolution filter, the following procedure is used. The first step in the procedure is linear interpolation. The values of new pixels $\beta_i$, with respect to the pixel values of the source image 11, are given by the following equations:

$$B_i = \frac{(n-i=+1)}{n} I_i + \frac{(i-1)}{n} I_2 \quad (1)$$

for i=1, ... n (n odd), and $$B_i = \frac{(n-i+0.5)}{n} I_i + \frac{(i-0.5)}{n} I_2 \quad (2)$$

for i=1, ... n (n even).

Using the linearly interpolated pixels $b_j$, (instances of Bj; i=1, 2, ... m) the m by 1 convolution filter is applied to obtain the output-pixel $O_k$. Therefore, the following expression for the output pixel $O_k$ is obtained:

$$O_i = \sum_{i=1}^{m} a_i b_i \quad (3)$$

where $a_i$ (i=1, ..., m) are the coefficients of the convolution filter. When the expressions for $b_i$ (i=1, ..., m), or the values of corresponding $B_{op}$ from equations (1) or (2), are substituted in equation (3), the following expression is obtained:

$$O_i = \sum_{i_1=1}^{i} \sum_{i_2=1}^{m} k_{i_1 i_2} a_{i_2} I_{i_1} \quad (4)$$

where $k_{ij}$ are the constant coefficients obtained by applying equations (1) or (2):

Using known expressions for bicubic interpolation, an alternate expression for the pixel value $O_k$ can be obtained:

$$O_k = \sum_{i=i}^{4} c_i I_i \quad (5)$$

where $c_i$ are the coefficients derived from the expressions for cubic interpolation in the case of magnification by n. Comparing equations (4) and (5), and equating coefficients with corresponding input pixels values $i_j$, the set of up to four linear equations for the coefficients $a_m$ of the filter is obtained:

$$\sum_{i_2=1}^{m} k_{i i_2} a_{i_2} = c_i \quad (6)$$

There can be less than four equations if the pixels obtained by bilinear interpolation used by the convolution filter do not have any contribution from some input pixels $i_j$. In that case, the number of equations is reduced by the number of such pixels.

The same procedure is repeated for the set of n consecutive output pixels $O_i$ (i=1, ..., n) that have different locations relative to the input pixels, and a system of linear equations for the convolution filter coefficients is obtained.

This system can be expressed in matrix form as:

$$C=KA \quad (7)$$

where C is the vector of corresponding coefficients $c_i$ from right sides of equations (6), K is the matrix of coefficients $K_{ij}$ of those linear equations, and A is vector of m filter coefficients $a_i$, (i=1, ..., m). For practical values of zoom factors n and filter sizes m this represents an overdetermined system of linear equations. In this case, the solution is determined by using the linear least squares method, and it has the form:

$$A=(K^T K)^{-1} K^T C \quad (8)$$

Upon determining the coefficients A of the convolution filter that is to be applied, the whole procedure for altering the spatial characteristics of a digital image is defined.

The second algorithm utilizes a two step procedure including bilinear interpolation followed by the application of a 2D convolution filter. The second algorithm can be applied for any integer magnification factor m, and for any 2D convolution filter size n.

As described above, the first step is bilinear interpolation. In the case of magnification by a factor n, there are $n^2$ pixels in the new, zoomed, image that have fundamentally different positions with respect to the pixels of the source image. The values of new pixels, $B_{ij}$, with respect to the pixel values of the source image, $I_{ij}$, are given by following equations:

$$B_{ij} = \frac{(n-i+1)(n-j+1)}{n^2}I_{11} + \frac{(n-i+1)(j-1)}{n^2}I_{12} + \frac{(i-1)(n-j+1)}{n^2}I_{21} + \frac{(i-1)(j-1)}{n^2}I_{22} \quad (9)$$

for i,j=1, . . . , n (n odd), and $$B_{ij} = \frac{(n-i+0.5)(n-j+0.5)}{n^2}I_{11} + \frac{(n-i+0.5)(j-0.5)}{n^2}I_{12} + \frac{(i-0.5)(n-j+0.5)}{n^2}I_{21} + \frac{(i-.05)(j-0.5)}{n^2}I_{22} \quad (10)$$

for i, j=1, . . . , n (n even). Values for $b_{ij}$ (instances of $B_{ij}$) can be calculated by using the expressions in equations (9) or (10) and substituting appropriate values for $I_{ij}$, i, and j depending on the position of $b_{ij}$ in the input image.

Using the bilinear interpolated pixels $b_{ij}$ (ij=1, 2, . . . , m) the m by m convolution filters applied to obtain the output pixels. The following expression for the output pixel $O_{ki}$ is obtained:

$$O_{ki} = \sum_{i=1}^{m}\sum_{j=1}^{m} a_{ij}b_{ij} \quad (11)$$

where $a_{ij}$ (i,j=1, . . . , m) are the coefficients of the convolution filter. If the expressions for $b_{ij}$, (i,j=1, . . . , m), or the values of the corresponding $B_{op}$ from equations (9) or (10), are substituted in equation (11), the following expressions are obtained:

$$O_{ki} = \sum_{i_1=1}^{j}\sum_{i_2=1}^{j}\sum_{i_3=1}^{m}\sum_{i_4=1}^{m} k_{i_1 i_2 i_3 i_4} a_{i_3 i_4} I_{i_1 i_2} \quad (12)$$

where a $k_{ijkl}$ are the constant coefficients obtained by applying equations (9) or (10).

Using known expressions for bicubic interpolation, the alternate expression for the pixel value $O_{ki}$ can be obtained:

$$O_l = \sum_{i=1}^{4}\sum_{i=j}^{4} c_{ij}I_{ij} \quad (13)$$

where $c_{ij}$ are the coefficients derived from the expressions for bicubic interpolation in the case of magnification by n. Comparing equations (12) and (13), and equating coefficients with corresponding input pixel values Iij, a set of up to sixteen linear equations for the filter coefficients $a_{mn}$, is obtained:

$$\sum_{i_3=1}^{m}\sum_{i_4=1}^{m} k_{ij i_3 i_4} a_{i_3 i_4} = c_{ij} \quad (14)$$

There can be less then sixteen equations if the pixels obtained by bilinear interpolation used by the convolution filter do not have any contribution from some input pixels $I_{ij}$. In that case, the number of equations is reduced by the number of such pixels. Repeating this procedure for all of the output pixels $O_{ij}$ (i,j=1, . . . , n) a system of linear equations for the convolution filter coefficients is obtained.

This system can be expressed in matrix form as:

$$C=KA \quad (15)$$

where C Is the vector of the corresponding coefficients $c_{ij}$ from right sides of equations (14), K is the matrix of coefficients $k_{ijkl}$ of those linear equations, and A is the vector of filter coefficients $a_{ij}$, (i,j=1, . . . , m). For practical values of zoom factors n and filter sizes m this represents an overdetermined system of linear equations. In this case, the solution is obtained using the linear least squares method and it has the form:

$$A=(K^TK)^{-1}K^TC \quad (16)$$

Upon determining the coefficients A of the convolution filter that is to be applied, the whole procedure for altering the spatial characteristics of a digital image is defined.

The above described interface provides the advantage of being easily understood and readily used with minimum training. In addition, the operator is provided with readily accessible information to facilitate performing the procedure.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A computed tomography system comprising an x-ray source, an x-ray detector aligned with said x-ray source, a processor coupled to said x-ray detector, and a display for displaying reconstructed images, said processor programmed to perform at least one of:
   generating a partially reconstructed image for display on said display; and
   dynamically reformatting images for display on said display;
   wherein to generate said partially reconstructed image, said processor is configured to weight data to provide a smooth transition from a first image to a next image.

2. A computed tomography system in accordance with claim 1 wherein said display is a wide angle flat panel display.

3. A computed tomography system in accordance with claim 1 wherein said processor overscan weights the data.

4. A computed tomography system in accordance with claim 1 wherein said image reformatting is performed utilizing image interpolation.

5. A computed tomography system in accordance with claim 1 further comprising a suspension system for suspending said display from a ceiling.

6. A computed tomography system in accordance with claim 1 wherein said display further comprises a user interface comprising an indicator for indicating x-ray exposure.

7. A computed tomography system in accordance with claim 6 wherein said indicator indicates at least one of x-ray exposure within a burst and x-ray exposure accumulated from multiple bursts.

8. A computed tomography system in accordance with claim 1 wherein said display comprises image controls, a messages section, and display controls.

9. A computed tomography system in accordance with claim 1 wherein said processor is further configured to magnify images for display.

10. A computed tomography system comprising an x-ray source, an x-ray detector aligned with said x-ray source, a processor coupled to said x-ray detector, and a display for displaying reconstructed images, said processor programmed to perform at least one of:

generating a partially reconstructed image for display on said display; and dynamically reformatting images for display on said display;

wherein said display comprises image controls, a messages section, and display controls, and wherein said display is controllable remotely.

11. A computed tomography system comprising an x-ray source, an x-ray detector aligned with said x-ray source, a processor coupled to said x-ray detector, and a display for displaying reconstructed images, said processor programmed to perform at least one of:

generating a partially reconstructed image for display on said display; and dynamically reformatting images for display on said display;

wherein said processor is further configured to magnify images for display, and wherein to magnify said images, said processor executes at least one of (a) a two pass algorithm in which each of the passes represents interpolation in the x and y directions respectively, and (b) a bilinear interpolation algorithm including a two dimensional convolution filter.

12. A computed tomography system comprising an x-ray source, an x-ray detector aligned with said x-ray source, a processor coupled to said x-ray detector, and a display for displaying reconstructed images, said processor configured to dynamically reformat images for display on said display;

wherein said processor is further configured to magnify images for display; and wherein to magnify said images, said processor executes at least one of (a) a two pass algorithm in which each of the passes represents interpolation in the x and y directions respectively, and (b) a bilinear interpolation algorithm including a two dimensional convolution filter.

13. A computed tomography system comprising an x-ray source, an x-ray detector aligned with said x-ray source, a processor coupled to said x-ray detector, and a display for displaying reconstructed images, said processor configured to generate a partially reconstructed image for display on said display, and to weight data to provide a smooth transition from a first image to a next image.

14. A computed tomography system in accordance with claim 13 wherein said processor is further configured to dynamically reformat images for display on said display wherein said image reformatting is performed utilizing image interpolation.

15. A computed tomography system in accordance with claim 13 wherein said processor is further configured to magnify images for display, and wherein to magnify said images, said processor executes at least one of (a) a two pass algorithm in which each of the passes represents interpolation in the x and y directions respectively, and (b) a bilinear interpolation algorithm including a two dimensional convolution filter.

16. A computed tomography system comprising an x-ray source, an x-ray detector aligned with said x-ray source, a processor coupled to said x-ray detector, and a display for displaying reconstructed images, said processor configured to dynamically reformat images for display on said display; and wherein said processor overscan weights the data.

17. A computed tomography system in accordance with claim 16 wherein said processor is further configured to magnify images for display.

18. A computed tomography system comprising an x-ray source, an x-ray detector aligned with said x-ray source, a processor coupled to said x-ray detector, and a display for displaying reconstructed images, said processor configured to dynamically reformat images for display on said display; and wherein said processor is further configured to generate a partially reconstructed image for display on said display, and to weight data to provide a smooth transition from a first image to a next image.

19. A computed tomography system in accordance with claim 18 wherein said image reformatting is performed utilizing image interpolation.

20. A computed tomography system in accordance with claim 19 wherein a plane for said image reformatting can be specified at any arbitrary angle.

* * * * *